United States Patent
Kobayashi et al.

(10) Patent No.: US 9,579,092 B2
(45) Date of Patent: Feb. 28, 2017

(54) POLYMER MOLDED BODY FOR PULLING BIOLOGICAL TISSUE, MEDICAL PULLING MEMBER USING SAME, AND MEDICAL PULLING TOOL

(76) Inventors: Kazutoshi Kobayashi, Ibaraki (JP); Kunihiro Suto, Ibaraki (JP); Makoto Nishimura, Tokyo (JP); Hiroto Kita, Tokyo (JP)

( * ) Notice: Subject to any disclaimer, the term of this patent is extended or adjusted under 35 U.S.C. 154(b) by 1087 days.

(21) Appl. No.: 13/639,607

(22) PCT Filed: Apr. 6, 2011

(86) PCT No.: PCT/JP2011/058724
§ 371 (c)(1),
(2), (4) Date: Nov. 2, 2012

(87) PCT Pub. No.: WO2011/126050
PCT Pub. Date: Oct. 13, 2011

(65) Prior Publication Data
US 2013/0053745 A1 Feb. 28, 2013

(30) Foreign Application Priority Data

Apr. 6, 2010 (JP) .................................. 2010-088205
Oct. 6, 2010 (JP) .................................. 2010-227052

(51) Int. Cl.
*A61F 5/00* (2006.01)
*A61B 17/02* (2006.01)
(Continued)

(52) U.S. Cl.
CPC ........ *A61B 17/0218* (2013.01); *A61B 1/0008* (2013.01); *A61B 2017/00269* (2013.01); *A61B 2017/00336* (2013.01)

(58) Field of Classification Search
CPC .............. A61B 17/0218; A61B 1/0008; A61B 2017/00269; A61B 2017/00336
(Continued)

(56) References Cited

U.S. PATENT DOCUMENTS

2009/0248055 A1* 10/2009 Spivey .............. A61B 17/32001
606/180

FOREIGN PATENT DOCUMENTS

EP    1 216 718      10/2004
JP    2002-320631    11/2002
(Continued)

OTHER PUBLICATIONS

Jonathan A. Kluge, et al., "Spider silks and their applications", Trends in Biotechnology, vol. 26, No. 5, pp. 244-251 (2008).
(Continued)

*Primary Examiner* — Pedro Philogene
*Assistant Examiner* — David C Comstock
(74) *Attorney, Agent, or Firm* — Fitch, Even, Tabin & Flannery, LLP

(57) ABSTRACT

According to a medical traction device containing a polymer molded article having biocompatibility as a weight for traction of a living tissue to be resected under observation with an endoscope, and a medical traction equipment containing the medical traction device and a grasping member connected to each other, such a medical traction device or traction equipment is provided that in ESD in a digestive tract, a dissected living tissue is efficiently removed from the operative field also in a direction that is different from the moving direction of the endoscope, thereby maintaining the field of view, and the procedures are thus performed safely and rapidly.

22 Claims, 14 Drawing Sheets

(51) Int. Cl.
*A61B 1/00* (2006.01)
*A61B 17/00* (2006.01)

(58) Field of Classification Search
USPC ............... 600/104, 114, 117, 132, 201, 204; 602/32, 36, 46
See application file for complete search history.

(56) References Cited

FOREIGN PATENT DOCUMENTS

| | | |
|---|---|---|
| JP | 2004-337490 | 12/2004 |
| JP | 2004-350735 | 12/2004 |
| JP | 2004-357816 | 12/2004 |
| JP | 2005-230 | 1/2005 |
| JP | 2005-386 | 1/2005 |
| JP | 2005-103107 | 4/2005 |
| JP | 2006-249115 | 9/2006 |
| JP | 2006-271832 | 10/2006 |
| JP | 2007-167400 | 7/2007 |
| JP | 2007-307000 | 11/2007 |
| JP | 2008-62004 | 3/2008 |
| JP | 2008-142516 | 6/2008 |
| JP | 2008-206972 | 9/2008 |
| WO | WO 92/19802 | 11/1992 |
| WO | WO 2008/149347 A2 | 12/2008 |

OTHER PUBLICATIONS

European Office Action mailed Jun. 26, 2015, for European Application No. 11765950.8, 7 pages.
Extended European Search Report dated Jul. 31, 2014, including Supplementary European Search Report and European Search Opinion, in connection with EP Application No. 11765950.8-1654/ 2556798 (PCT/JP2011/058724).
Machine translation of Japanese Application No. 2006-249115.

* cited by examiner

POLYMER MOLDED BODY FOR PULLING BIOLOGICAL TISSUE, MEDICAL PULLING MEMBER USING SAME, AND MEDICAL PULLING TOOL

TECHNICAL FIELD

The present invention relates to a polymer molded article, and a medical traction device and a medical traction equipment using the same, and more specifically relates to a polymer molded article for traction of a living tissue, such as mucosa and tumor, dissected in an endoscopic surgery, for example, endoscopic submucosal dissection (hereinafter referred to as ESD), and a medical traction device and a medical traction equipment using the same.

BACKGROUND ART

A tumor, such as a polyp and an early cancer, formed in a mucosa of a digestive tract, such as a stomach and a large intestine, can be now resected by an endoscopic surgery using endoscopic mucosal resection (EMR) and ESD without abdominal section. In particular, a flat tumor and a large tumor having a size of several centimeter are difficult to process by EMR, and can now be efficiently resected by employing ESD. Ordinary ESD is performed in the following procedures.

(1) The circumference of the lesion is marked.
(2) A local injection drug, such as physiological saline or a hyaluronic acid aqueous solution, is injected the submucosal layer for prominence.
(3) The circumference of the lesion is cut with a knife.
(4) The submucosal layer is dissected.
(5) The tumor is recovered.

In the procedure (4), however, the mucosa to be resected may cover the field of view, and the dissected mucosa may be readhered, in some cases, which may cause prolongation of the procedure time. Furthermore, the field of view may not be sufficiently maintained, which concerns about bleeding due to damage of a blood vessel and perforation of a muscular wall.

For solving the problems, various mucosal resection and dissection assisting tools for removing the resected mucosa from the processed area, such as medical grasping equipments and medical traction equipments, have been proposed (see Patent Documents 1 to 5).

However, the traction with a magnetic anchor involves such problems that a large-size equipment is required for traction, movement of the magnetic anchor inside the digestive tract may damage the mucosa (Patent Document 1).

In the method, in which a clip is attached to the other mucosal portion than a lesion, to which a clip and a spring traction device attached to the mucosa of the lesion are connected, thereby resecting the submucosal layer of the mucosa of the lesion, it is necessary to attach the clip to the normal mucosa portion, which damages the unlesioned portion. Furthermore, the lesion and the mucosa on the opposite side are attracted to each other, which concerns about narrowing the operative field (see Patent Documents 2 to 4).

In the case where a mucosal resection and dissection assisting tool that is introduced beside the endoscope, it is necessary to introduce plural tubes into the narrow digestive tract, which may concern about an operational error of the endoscope. Furthermore, there is a concern that the assisting tool may be erroneously moved during operation of the endoscope, which may bring about troubles in the traction operation. Moreover, the assisting tool can be moved only in the same direction as the endoscope, which restrict the direction of opening the mucosa, and it cannot be moved during the endoscopic operation in a direction that is different from the moving axis of the endoscope (see Patent Document 5).

RELATED ART DOCUMENTS

Patent Documents

[Patent Document 1] JP-A-2004-337490
[Patent Document 2] JP-A-2005-103107
[Patent Document 3] JP-A-2008-62004
[Patent Document 4] JP-A-2008-142516
[Patent Document 5] JP-A-2007-307000

SUMMARY OF THE INVENTION

Problems to be Solved by the Invention

In view of the problems, an object of the present invention is to provide such a mucosal resection and dissection assisting tool that in ESD in a digestive tract, a dissected living tissue is efficiently removed from the operative field also in a direction that is different from the moving direction of the endoscope, thereby maintaining the field of view, and the procedures are thus performed safely and rapidly.

Means for Solving the Problems

As a result of earnest investigations made by the present inventors, it has been found that the problems are solved by using, as a mucosal resection and dissection assisting tool, a polymer molded article that functions as a weight for traction of a living tissue to be resected under observation with an endoscope. The present invention has been completed based on the knowledge.

The present invention provides a polymer molded article that is a weight for traction of a living tissue to be resected under observation with an endoscope, and a medical traction device and a medical traction equipment containing the polymer molded article.

Advantages of the Invention

By using the polymer molded article or a medical traction device or equipment according to the present invention, on resecting a living tissue, such as a tumor formed in a mucosa in a digestive tract, by ESD, traction of the resected living tissue may be properly conducted, thereby performing ESD safely and rapidly.

EMBODIMENTS FOR CARRYING OUT THE INVENTION

The polymer molded article of the present invention functions as a weight for traction of a living tissue to be resected under observation with an endoscope, and more specifically, exhibits the function thereof on using as a constitutional element of a medical traction device. The present invention also includes a medical traction equipment that contains the medical traction device and a grasping member for grasping a living tissue.

Figure 8:
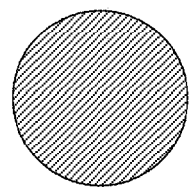
FIG. 8 is a schematic illustration of a polymer molded article according to the present invention.
Figure 9:
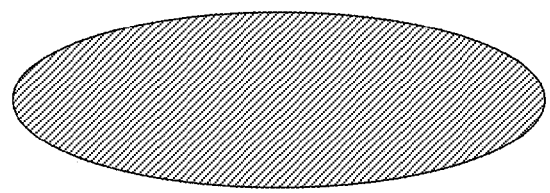
FIG. 9 is a schematic illustration of a polymer molded article according to the present invention.
Figure 10:
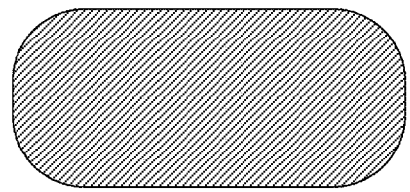
FIG. 10 is a schematic illustration of a polymer molded article according to the present invention.
Figure 11:
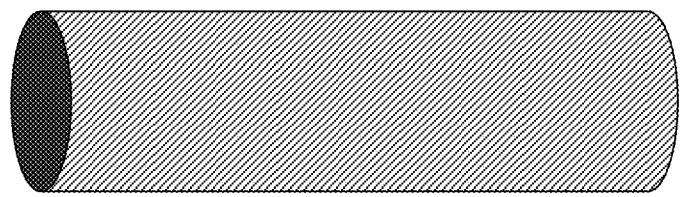
FIG. 11 is a schematic illustration of a polymer molded article according to the present invention.

The shape of the polymer molded article of the present invention is not particularly limited. Specific examples thereof include a spherical shape (FIG. 8), an ellipsoidal shape (FIG. 9), a rotational solid of a rectangle with round edges (rectangular parallelepiped with round edges) (FIG. 10), a cylindrical columnar shape (FIG. 11), a conical shape (not shown in the figures), a polyhedral shape (not shown in the figures), cubic shape (not shown in the figures), and a rectangular parallelepiped (not shown in the figures). A shape with less edges, such as a spherical shape, an ellipsoidal shape and a polyhedral shape, is preferred for preventing engagement from occurring on passing through a narrowed portion in a digestive tract. The processing method of the polymer molded article is not particularly limited, and examples thereof include cutting with a machining center, and cutting with scissors, a knife or the like, by which the polymer molded article may be produced. In alternative, the polymer molded article having an arbitrary shape may be produced by using an arbitrary mold on molding the same.

The size of the polymer molded article 11 is preferably from 5 to 100 mm in terms of the maximum length. When the size of the polymer molded article 11 is 5 mm or more, it may be easily connected to a connecting member 22 and may have a weight that is sufficient for traction of a living tissue. When the size of the polymer molded article 11 is 100 mm or less, a sufficient space may be obtained on conducting traction inside a digestive tract. In view of the factors, the size of the polymer molded article is more preferably from 7 to 50 mm, and further preferably from 10 to 30 mm.

The polymer molded article 11 of the present invention preferably has elasticity for introducing through a forceps port of an endoscope, and for preventing an inner wall of a digestive tract from being damaged on introducing the polymer molded article disposed at the distal end of the endoscope into the digestive tract. Preferred examples thereof include a rubber-like polymer molded article.

The polymer molded article having elasticity may not be necessarily formed of a substance that has sufficient elasticity, but may have an elastic structure with a porous material, a hollow shape or the like. Furthermore, the elastic body may be provided by disposing the elastic substance or the elastic structure locally at the surface or the interior thereof.

In the present invention, the polymer molded article preferably has a 25% compression hardness of from 0.01 to 50 N. When the 25% compression hardness is 0.01 N or more, the shape thereof may be maintained on being in contact with the inner wall of the digestive tract, and when it is 50 N or less, the polymer molded article is sufficiently deformed and passed through a narrowed portion without damaging a living tissue, such as a mucosa. In view of the factors, the 25% compression hardness of the polymer molded article is more preferably from 0.1 to 20 N, and further preferably from 0.5 to 5 N.

The 25% compression hardness herein is measured in the following manner. A fibroin porous article thus obtained is allowed to stand in pure water for one day for complete water absorption, and the hardness thereof is measured with a compression tester. The compression tester used is EZ Test, produced by Shimadzu Corporation, with load cells of 10 N and 50 N and a load plate of 8 mm in diameter. The porous article is compressed to 25% of the initial thickness at a speed of 1 mm/min, and the load (N) applied thereon is read and designated as the 25% compression hardness.

In the present invention, the polymer molded article preferably has a 40% compression residual strain of from 1 to 35%, more preferably from 1 to 20%, and further preferably from 1 to 10%. When the 40% compression residual strain is 35% or less, the polymer molded article may sufficiently restore the size thereof after deformation in the narrowed portion in the digestive tract.

The 40% compression residual strain herein is measured in the following manner. A fibroin porous article (thickness: 10 mm, 30 mm in length×60 mm in width) thus obtained is allowed to stand in pure water for one day for complete water absorption, and after compressing to 40% with a compression tester, the restored thickness is measured. The compression tester used is EZ Test, produced by Shimadzu Corporation, with a compression jig with a circular shape having a diameter of 8 mm. The porous article is compressed to 40% of the initial thickness at a speed of 1 mm/min, followed by maintaining for 5 minutes. The article is then released from the compression state and allowed to stand in the air or pure water for 5 minutes, and the thickness (D) of the porous article is measured. The compression residual strain is calculated from the change of the thickness according to the following expression.

$$\text{compression residual strain (\%)} = (10-D) \times 100/10$$

It is important that the polymer molded article of the present invention functions as an elastic body and changes the volume thereof for passing through the forceps port of the endoscope and the narrowed portion in the digestive tract on introducing into the digestive tract. The polymer molded article has a role of a weight as a traction device, and for functioning as a weight after introducing into the digestive tract, the polymer molded article necessarily has a weight that is capable of conducting traction of a living tissue. For achieving both the elastic body and the function of a weight, a porous article is preferably used. Specifically, the use of a porous article provides elasticity on introducing into the digestive tract, and after introducing into the digestive tract, the weight thereof may be easily controlled through absorption of water to the porous article.

In the case where the polymer molded article is porous, a porous article having a high water absorption coefficient is preferably used for control the weight thereof easily. More specifically, the water absorption coefficient thereof is preferably such a value that water in an amount of from 200 to 10,000% by mass of the own weight can be absorbed. When the water absorption coefficient is 200% by mass or more, the porous article may be imparted with a sufficient weight, and when it is 10,000% by mass or less, the porous article may have a sufficient strength for the use of the porous article as a traction device. In view of the factors, the water absorption coefficient of the polymer molded article is more preferably from 400 to 8,000% by mass, and further preferably from 600 to 6,000% by mass.

The water absorption coefficient of the porous article may be measured in the following manner. A porous article is shaped into 30×30×18 mm, which is used as a specimen for measurement. The porous article having been sufficiently dried is measured for a dry weight (Wa). The porous article is immersed in ultrapure water without collapse for total water absorption, and the weight thereof is measured (Wb). The water absorption coefficient is calculated from these values according to the following expression.

$$\text{water absorption coefficient (\%)} = (Wb-Wa) \times 100/Wa$$

The polymer molded article preferably has a sufficiently large water absorbing rate for controlling the weight thereof rapidly in a short period of time inside the digestive tract. The water absorbing rate in the present invention is in accordance with the Pyrex method in JISL 1907. That is, five test pieces each having a dimension of 150×10 mm are measured for the length of the maximum attained position and the length of the minimum attained position after standing for 3 minutes, and the average value of the five specimens is designated as a water height, which is used as an index of the water absorbing rate. More specifically, the water height is preferably from 5 to 150 mm. When the water height is 5 mm or more, the weight may be rapidly controlled in the digestive tract. In view of the factors, the water height of the polymer molded article is more preferably 10 mm or more, and further preferably 20 mm or more.

The polymer molded article of the present invention preferably has a large water retention rate for retaining absorbed water. A large water retention rate prevents water from flowing out during the traction operation, thereby preventing the weight from being fluctuated. More specifically, the water retention rate is preferably from 85 to 100%. When the water retention rate is 85% or more, such a concern may be diminished that water flows out during the traction to change the weight thereof, which troubles the operation. In view of the factors, the water retention rate of the polymer molded article is more preferably from 87 to 100%, and further preferably from 90 to 100%.

The water retention rate herein is measured in the following manner. A porous article is shaped into 60×30×20 mm, which is used as a specimen for measurement. The porous article having been sufficiently immersed in pure water is measured for weight (Wc). The porous article is again sufficiently immersed in pure water and placed on a glass flat plate (MSA Coat Microslideglass, produced by Matsunami Glass Industries, Ltd. 76×52 mm), which is wetted with pure water on the surface thereof and inclined at 45°, for 10 minutes in such a manner that the largest plane (60×30 mm plane) thereof faces downward, and the longitudinal direction thereof is directed to the inclined direction. Thereafter, the weight of the porous article is measured (Wd).

$$\text{water retention rate (\%)} = 100 - (Wc-Wd) \times 100/(Wc)$$

It is important that the composition of the polymer molded article is a polymer having biocompatibility. Examples thereof include polymers formed of a silicone resin; a synthetic polymer, such as polylactic acid, polycaprolactone, polyvinyl alcohol, nylon, polypropylene, polyethylene and polyethylene terephthalate; a protein, such as silk sericin, silk fibroin, casein, keratin, collagen and starch; and a polysaccharide, such as hyaluronic acid, chitosan and cellulose, but are not limited these materials. Among these, silk fibroin, which is known to be safe as a suture thread and a food additive, is preferred.

As an example of the polymer molded article of the present invention, a polymer molded article as a porous article formed of silk fibroin as a preferred material (which is hereinafter referred to as a silk porous article) will be described below.

A silk porous article that is preferably used in the present invention may contain silk fibroin and depending on necessity an additive having an effect of facilitating formation of the porous article.

The silk fibroin used in the present invention may be any one of products produced from a natural silkworm, such as a domesticated silkworm, a wild silkworm and a Japanese oak silkworm, and a transgenic silkworm, and the production method thereof is not limited. In consideration of simplicity in the production process, a product produced from a domesticated silkworm is preferred. In the present invention, the silk fibroin is preferably used in the form of an aqueous solution, and a method of providing a silk fibroin aqueous solution used may be any known method.

Preferred examples of the method include a method of dissolving the silk fibroin in a lithium bromide aqueous solution with high concentration since the silk fibroin is poor in solubility in water, and then subjecting the solution to desalting by dialysis. The method of controlling the concentration of the silk fibroin in the aqueous solution is preferably a method of concentrating by air drying due to the simplicity thereof.

The amount of the silk fibroin mixed in the present invention is preferably from 0.1 to 40% by mass in the silk fibroin aqueous solution having the additive added thereto. When the amount is in the range, a porous article having a sufficient strength as the polymer molded article may be produced. In view of the factors, the amount of the silk fibroin mixed is more preferably from 0.5 to 20% by mass, and further preferably from 1 to 12% by mass.

The additive used in the present invention has an effect of facilitating formation of the porous article, and specific examples thereof include an organic solvent, an amino acid and an aliphatic carboxylic acid, which may be used solely or as a combination of two or more kinds thereof.

The amount of the additive added is preferably from 0.01 to 18% by mass in the silk fibroin aqueous solution having the additive added thereto. When the amount is in the range, a porous article having a sufficient strength as the polymer molded article, which is a weight for traction of a living tissue to be resected under observation with an endoscope, may be produced. In view of the factors, the amount of the additive added is more preferably from 0.1 to 5% by mass. In view of the same factors, the amount of the additive added is preferably from 1 to 500 parts by mass, more preferably from 5 to 50 parts by mass, and further preferably from 10 to 30 parts by mass, per 100 parts by mass of the silk fibroin.

Examples of the organic solvent used in the present invention include methanol, ethanol, isopropanol, butanol, glycerol, dimethylsulfoxide (DMSO), dimethylformamide (DMF), pyridine, acetone and acetonitrile. Among these, ethanol is preferred from the standpoint of the strength of the silk porous article obtained and the safety of the additive to the living body.

Examples of the amino acid used in the present invention include an aliphatic amino acid, such as a monoaminocarboxylic acid, e.g., valine, leucine, isoleucine, glycine, alanine, serine, threonine and methionine, a monoaminodicarboxylic acid (an acidic amino acid), e.g., asparaginic acid and glutamic acid, an aliphatic amino acid, and a diaminocarboxylic acid, e.g., glutamine; an aromatic amino acid, such as phenylalanine and tyrosine; and an amino acid having a heterocyclic ring, such as proline, hydroxyproline and tryptophan, and among these, an acidic amino acid and an oxyamino acid, such as hydroxyproline, serine and threonine, are preferred from the standpoint of the easiness in controlling the form and the properties.

In view of the same factors, in the acidic amino acid, a monoaminodicarboxylic acid is preferred, and asparaginic acid and glutamic acid are more preferred, and in the oxyamino acid, hydroxyproline is more preferred.

An amino acid includes an L-optical isomer and a D-optical isomer, and in the present invention, both the L-isomer and the D-isomer may be used since there is no difference in the resulting porous article between them.

Among these, L-asparaginic acid, L-glutamic acid and L-hydroxyproline are preferred from the standpoint of the strength of the resulting silk porous article.

Preferred examples of the aliphatic carboxylic acid used in the present invention include a saturated or unsaturated monocarboxylic, dicarboxylic or tricarboxylic acid having from 1 to 6 carbon atoms, and examples thereof include formic acid, acetic acid, propionic acid, butyric acid, succinic acid, lactic acid, acrylic acid, 2-butenoic acid and 3-butenoic acid. The aliphatic carboxylic acid used in the present invention preferably has pKa of 5.0 or less, more preferably from 3.0 to 5.0, and further preferably from 3.5 to 5.0.

Among these, lactic acid, succinic acid and acetic acid are particularly preferred from the standpoint of the strength of the resulting silk porous article and the safety of the additive to the living body.

The additive used in the present invention is preferably used in the form of an aqueous solution from the standpoint of preventing deposition of the silk fibroin due to stirring or heating conducted on adding the additive to the silk fibroin aqueous solution. In the case where an additive that has low solubility in water is used in the present invention, such an aqueous solution of the additive is preferably used that is produced by adding and dissolving the additive in heated water, and then cooled to 30° C. or lower. In the case where the additive is deposited in the course of cooling, the deposited additive is preferably removed by filtering or the like. In view of the factors, the additive used in the present invention is preferably a water soluble additive.

The silk porous article used as the polymer molded article of the present invention may be obtained, for example, in such a manner that a silk fibroin aqueous solution, to which an aqueous solution of an additive is added and mixed depending on necessity, is poured into a vessel, frozen, and then melted.

The amount of the additive added is as described above, and the freezing temperature is not particularly limited as far as it is a temperature, at which the silk fibroin aqueous solution having the additive added thereto is frozen, and is preferably approximately from −1 to −40° C., more preferably approximately from −5 to −40° C., and further preferably from −10 to −30° C.

The freezing time is preferably 2 hours or more, and more preferably 4 hours or more, for freezing sufficiently the silk fibroin aqueous solution having the additive added thereto, and maintaining the frozen state for a certain period of time.

In the freezing method, the silk fibroin aqueous solution having the additive added thereto may be frozen by decreasing the temperature at once to the freezing temperature, but for providing a silk porous article having a uniform structure, it is preferred that before freezing, the silk fibroin aqueous solution having the additive added thereto is maintained once at a temperature of approximately from 4 to −9° C., and preferably approximately from 0 to −5° C., for 30 minutes or more to make the content of the vessel uniform, and then the temperature is decreased to the freezing temperature for freezing. Furthermore, in the case where the temperature to be maintained is approximately from −1 to −9° C., and preferably from −1 to −5° C., the silk fibroin aqueous solution is at a temperature providing a supercooled state (i.e., a supercooling temperature) before freezing, and thereby a silk porous article having a more uniform structure may be obtained. A silk porous article having a further uniform structure may be obtained, and the structure and the strength of the porous article may be controlled in a certain extent, in such a manner that the period of time of maintaining the supercooling temperature is controlled, the temperature gradient on decreasing the temperature from the supercooling temperature to the freezing temperature is controlled, and the like measures.

Subsequently, the frozen silk fibroin aqueous solution is then melted to provide a silk porous article. The method of melting is not particularly limited, and examples thereof include spontaneous melting and storage in a thermostat chamber.

As a method of controlling the concentration of the additive contained in the resulting silk porous article after producing the silk porous article, for example, the silk porous article may be immersed in pure water for dialysis, which is one of the most convenient methods. In alternative, in the case where the additive is in a liquid state at room temperature, the silk porous article may be freeze-dried, whereby removing the additive and water simultaneously.

As a method of controlling the water concentration after producing the silk porous article, for example, the silk porous article may be dried for evaporating water. Examples of the method of drying include spontaneous drying, freeze drying and heat drying, and freeze drying is preferred since shrinkage on drying can be suppressed.

The silk porous article used as the polymer molded article of the present invention has a sponge structure, and in general, the porous article contains water and is a flexible structure in a hydrated state unless water is removed therefrom by freeze drying or the like.

The silk porous material of the present invention may have a size of pores (i.e., a pore diameter) of approximately from 10 to 300 μm, which may be controlled to a certain extent through the mixing ratio of the silk fibroin and the additive and the conditions of the cooling process on freezing as described above, and may be determined depending on the purpose.

The medical traction device of the present invention will be described. The medical traction device of the present invention has at least one polymer molded article that functions as a weight. The medical traction device of the present invention preferably has at least one of a first connecting member, a second connecting member and a third connecting member. In the description, a connecting member that connects the polymer molded article directly to a living tissue, and a connecting member that connects the polymer molded article to a grasping member in an embodiment where the polymer molded article and a living tissue are connected indirectly to each other through the grasping member for grasping the living tissue are referred to as the first connecting member. A connecting member that connects the polymer molded article to an endoscope is referred to as the second connecting member, and a connecting member that connects the plural polymer molded articles is referred to as the third connecting member. The simple term "connecting member" means all the first to third connecting members, and referrers to matters that are common to the members.

The shape of the connecting member used in the present invention is preferably an elongated shape in a thread form. For example, the polymer molded article is preferably connected with a connecting member, such as a silk thread and nylon as a suture.

The first connecting member and the second and third connecting members may be formed of the same materials or different materials. The first to third connecting members may be connected through a common material, such as one silk thread, or may form separate connecting members independently.

Figure 12:
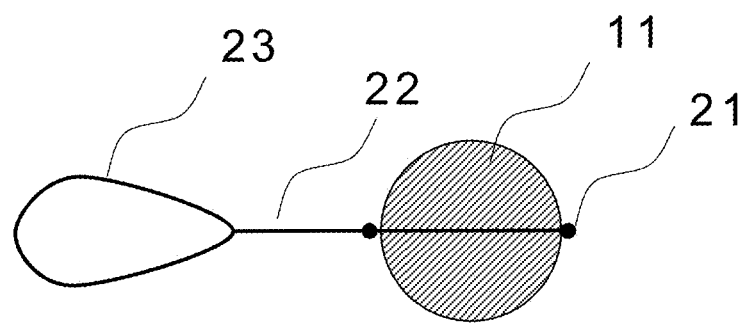
FIG. 12 is a schematic illustration showing a medical traction device according to the present invention.

The medical traction device of the present invention will be described with reference to FIGS. 12 to 24. The medical traction device of the present invention has at least one polymer molded article, which is a weight for traction of a living tissue to be resected under observation with an endoscope. FIG. 12 shows an example having one polymer molded article, and FIGS. 13 to 24 show examples each having plural polymer molded articles. FIGS. 12 to 15 and 20 to 24 show examples each having a spherical polymer molded article, FIGS. 16 and 17 show examples each having an ellipsoidal polymer molded article, FIG. 18 shows an example having a cubic polymer molded article, and FIG. 19 shows an example having a cylindrical columnar polymer molded article.

As shown in FIG. 12, the medical traction device 1 of the present invention has a spherical polymer molded article 11, and preferably has at least one of a first connecting member that connects the polymer molded article 11 directly or indirectly to a living tissue and a second connecting member that connects the polymer molded article 11 directly or indirectly to an endoscope. The connecting member 22 shown in FIG. 12 may be used any of the first connecting member, the second connecting member, and a first and second connecting member, which has both the functions thereof. In the case where the connecting member 22 is used as the first connecting member, the connecting member may be used as a connecting member that connects the polymer molded article 11 to a grasping member for grasping a living tissue.

Figure 13:
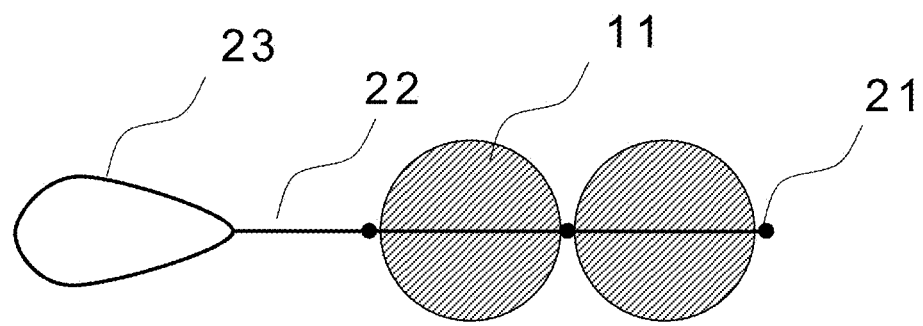
FIG. 13 is a schematic illustration showing a medical traction device according to the present invention.
Figure 14:
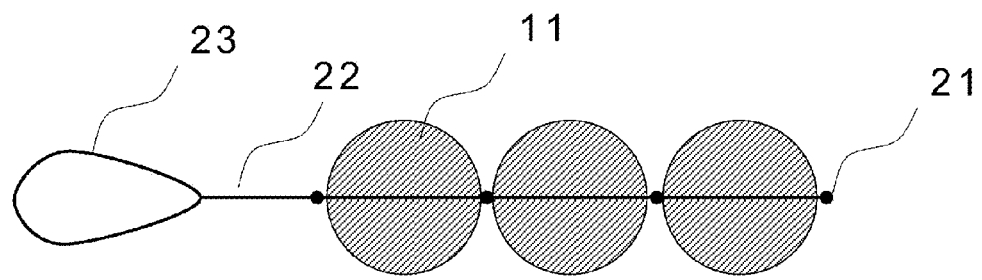
FIG. 14 is a schematic illustration showing a medical traction device according to the present invention.
Figure 15:
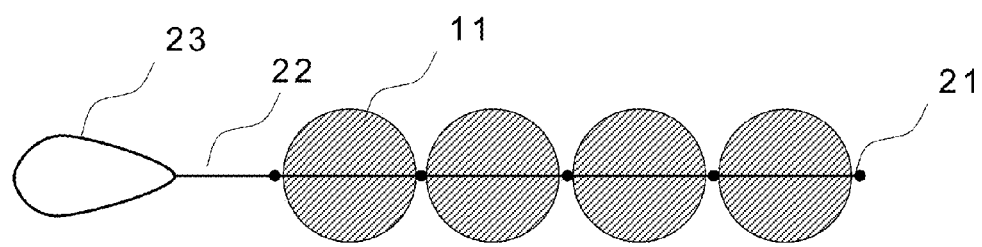
FIG. 15 is a schematic illustration showing a medical traction device according to the present invention.
Figure 16:
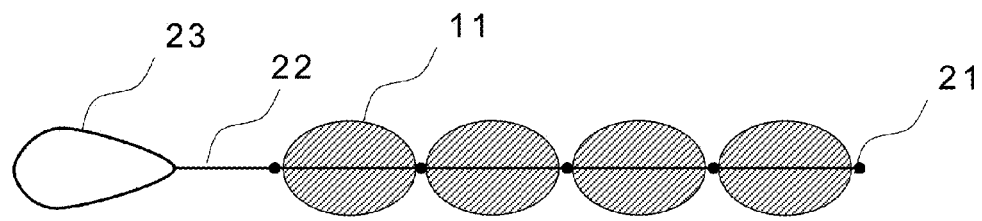
FIG. 16 is a schematic illustration showing a medical traction device according to the present invention.
Figure 17:
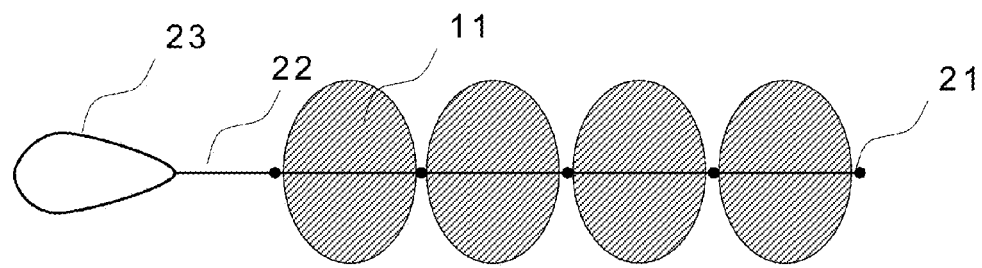
FIG. 17 is a schematic illustration showing a medical traction device according to the present invention.
Figure 18:
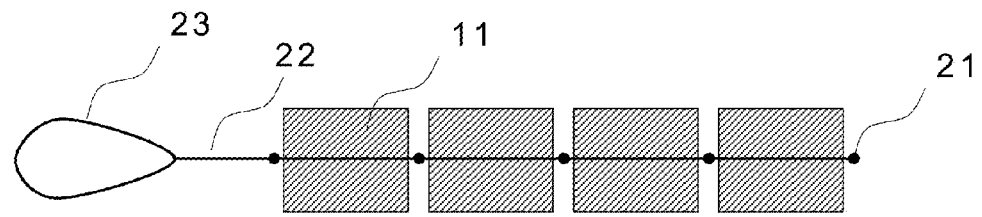
FIG. 18 is a schematic illustration showing a medical traction device according to the present invention.
Figure 19:
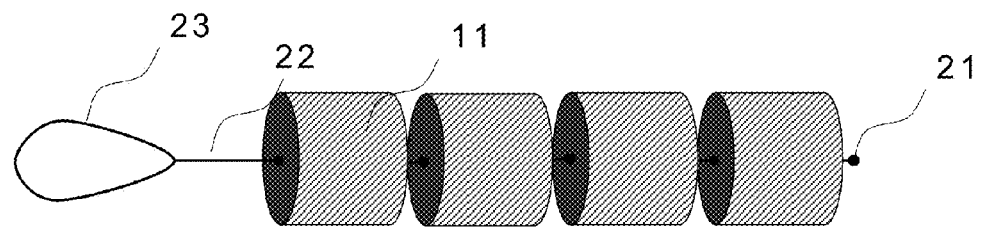
FIG. 19 is a schematic illustration showing a medical traction device according to the present invention.
Figure 20:
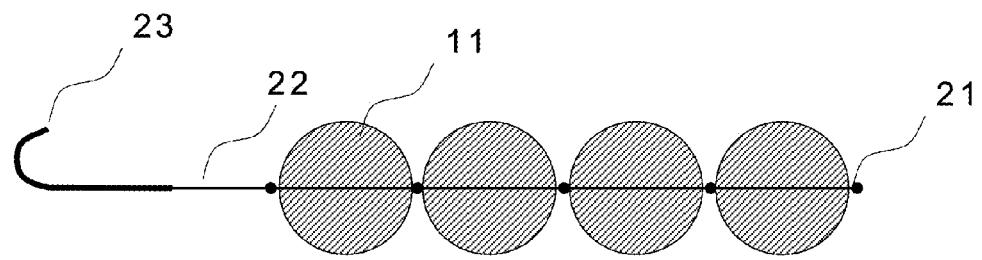
FIG. 20 is a schematic illustration showing a medical traction device according to the present invention.

The medical traction device of the present invention may have two or more polymer molded articles, and in general, as shown in FIGS. 13 to 24, the polymer molded articles are used after connecting with the third connecting member 22. FIGS. 13 and 14 show embodiments having two polymer molded articles 11 and three polymer molded articles 11, respectively, and FIGS. 15 to 24 show embodiments each having four polymer molded articles 11. The third connecting member 22 shown in FIGS. 13 to 24 may be used as a first and third connecting member, which also functions as the first connecting member, may be used as a second and third connecting member, which also functions as the second connecting member, and may be used as a first, second and third connecting member, which functions as all the three members.

The connecting member 22 in the present invention may have a mechanism that prevents the polymer molded article 11 from being dropped off from the traction device (i.e., a drop-off prevention mechanism). For example, a knot as a fastener 21, a washer 24, a fastener or the like for fastening the polymer molded article may be inserted at the back or the front and back of the polymer molded article. Examples of the material for the fastener 21 include plastics, such as polyethylene, polypropylene, polyethylene terephthalate, silicone and nylon, a metal, such as titanium and stainless steel, and a biologically derived material, such as a silk thread, silk fibroin, silk sericin, pullulan, gelatin, chitosan, starch, cellulose and alginic acid. In the fastener, a molded article or the like in the form of a bar, a circle, a sphere or the like may be disposed at the knot.

Figure 32:
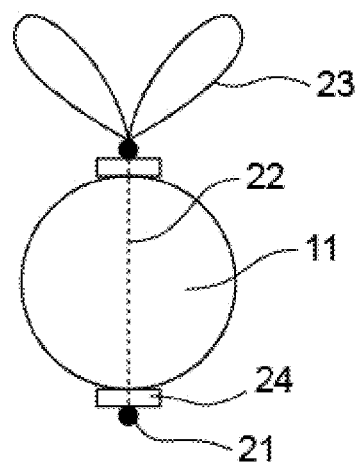
FIG. 32 is a schematic illustration showing a medical traction device according to the present invention.

For example, as shown in FIG. 32, a connecting member 22 formed of a suture may be placed through the center of the spherical polymer molded article 11 formed of a fibroin porous article, with washers 24 and knots disposed as a fastener 21, with which the polymer molded article 11 may be prevented from being dropped off, and two connecting portions 23 may be disposed on the upper side thereof.

The polymer molded article may have a through hole, through which the connecting member 22 is placed. The through hole preferably has a cylindrical shape but may be any shape that is capable of placing the connecting member 22 therein. The cylindrical shape may be used only after forming the through hole in the polymer molded article, but a cylindrical tube 25 may be disposed therein. The use of the tube 25 disposed prevents the polymer molded article from being damaged with the connecting member 22. Examples of the material for the tube 25 include plastics, such as polyethylene, polypropylene, polyethylene terephthalate, silicone and nylon, a metal, such as titanium and stainless steel, and a biologically derived material, such as a silk thread, silk fibroin, silk sericin, pullulan, gelatin, chitosan, starch, cellulose and alginic acid.

Figure 33:
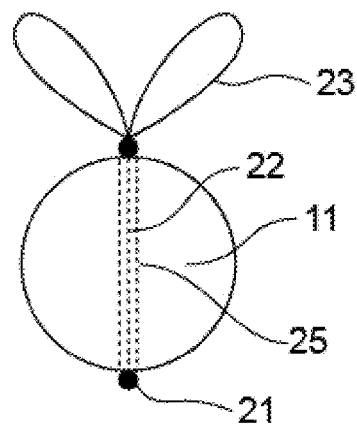
FIG. 33 is a schematic illustration showing a medical traction device according to the present invention.

For example, as shown in FIG. 33, a tube 25 may be placed through the center of the spherical polymer molded article 11 formed of a fibroin porous article for preventing the polymer molded article from being damaged.

The medical traction device of the present invention preferably has a connecting portion. The connecting portion is not particularly limited as far as it has such a structure that is capable of being connected to a living tissue directly or through a grasping member, such as forceps, for which various forms may be used, such as a string shape, a loop shape and hook shape, and the connecting portion is preferably provided.

The connecting member 22 in the medical traction device of the present invention may have at one end thereof one or plural portion in the form of a loop (ring) or a hook, and may have both a portion in the form of a loop and a portion in the form of a hook. The portions in these forms may be used as a connecting portion for connecting the polymer molded article 11 directly or indirectly to a living tissue, or a connecting portion for connecting the polymer molded article 11 to an endoscope. In the case where plural connecting portions are provided, they may be the same as or different from each other.

At least one of the aforementioned connecting portions may be used for both a connecting portion for connecting directly or indirectly to a living tissue and a connecting portion for connecting to an endoscope. For example, it may be used as a connecting portion for connecting to an endoscope until reaching the operative field, and then may be detached from the endoscope for using as a connoting portion for connecting directly or indirectly to a living tissue. In the case where plural connecting portions are provided, at least one among these may be used a connecting portion to an endoscope, and at least one of the balance thereof may be used as a connoting portion for connecting directly or indirectly to a living tissue.

The connecting member 22 in the present invention may have a drop-off prevention mechanism and both a portion in the form of a loop and a portion in the form of a hook.

Figure 21:
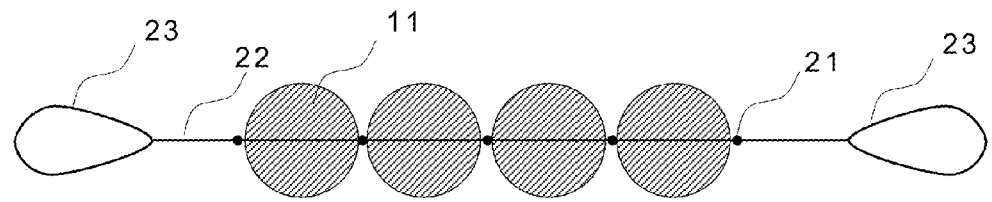
FIG. 21 is a schematic illustration showing a medical traction device according to the present invention.
Figure 22:
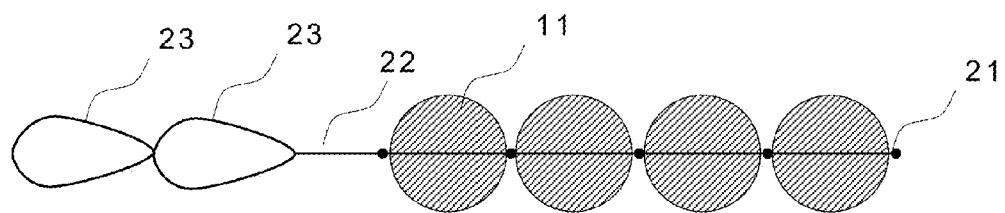
FIG. 22 is a schematic illustration showing a medical traction device according to the present invention.
Figure 23:
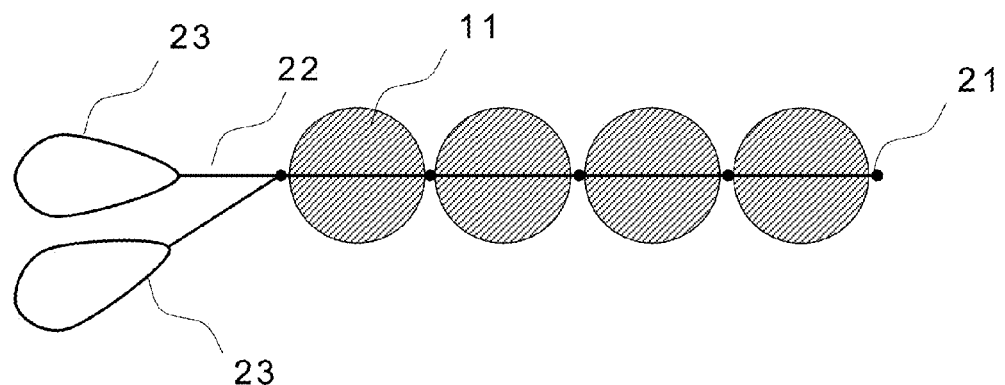
FIG. 23 is a schematic illustration showing a medical traction device according to the present invention.
Figure 24:
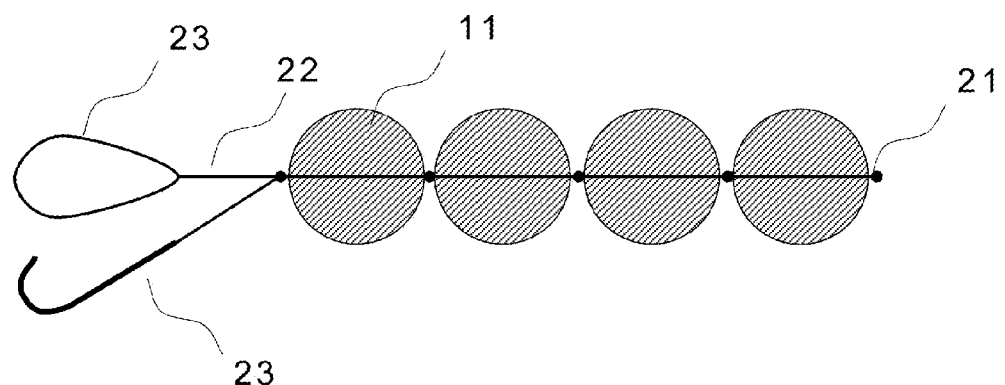
FIG. 24 is a schematic illustration showing a medical traction device according to the present invention.

In the examples shown in FIGS. 12 to 19, a fastener 21 as the drop-off prevention mechanism is provided at one end of the connecting member 22, and a portion in the form of a loop 23 is provided at the other end thereof. In the example shown in FIG. 20, a fastener 21 as the drop-off prevention mechanism is provided at one end of the connecting member 22, and a portion in the form of a hook 23 is provided at the other end thereof. In the example shown in FIG. 21, a fastener 21 as the drop-off prevention mechanism is provided in the intermediate part of the connecting member 22, and a portion in the form of a loop 23 is provided at both ends thereof. In the case where a portion in the form of a loop 23 as a connecting portion is provided at both ends as shown in FIG. 21, the pair of connecting portions may be connected to two grasping members, such as forceps, that are connected to mucosae to be resected from two different positions respectively, and thereby a wider field of view may be obtained even on resecting a larger tumor. Furthermore, plural connecting portions 23 may be provided (see FIGS. 22 to 24), and a branched connecting portion 23 may be provided (see FIGS. 23 and 24). In the examples shown in FIGS. 22 and 23, a fastener 21 as the drop-off prevention mechanism is provided at one end of the connecting member 22, and plural (two) portions in the form of a loop 23 is provided at the other end thereof. In the example shown in FIG. 22, the two portions in the form of a loop are formed continuously, and in the examples shown in FIG. 23, the two portions in the form of a loop are provided and branched from each other. In the example shown in FIG. 24, a fastener 21 as the drop-off prevention mechanism is provided at one end of the connecting member 22, and a portion in the form of a loop 23 and a portion in the form of a hook 23 are provided and branched from each other.

In an embodiment where plural polymer molded articles are provided, the weight may be arbitrarily controlled by cutting the connecting member 22 (i.e., the third connecting member) between the polymer molding articles or the end knot (i.e., the fastener 21). For example, as shown in FIG. 15, by cutting the end knot (i.e., the fastener 21) or the position at the front thereof, only the polymer molded article 11 at the right end may be dropped off, thereby providing a weight with three polymer molded articles easily. One or more knots may be provided between the polymer molded articles. In the case where two or more knots are provided, for example, it is preferred that the connecting member 22 between the polymer molded articles has a drop-off prevention mechanism, such as a knot (i.e., the fastener 21), and thereby the polymer molded article at the front of the drop-off prevention mechanism by cutting at the position at the back thereof. For example, as shown in FIG. 15, there is such an advantage that by cutting the intermediate knot (i.e., the fastener 21) or the position at the front thereof, the cutting operation of the polymer molded articles may be completed while the polymer molded articles at the front thereof is retained but not dropped off, thereby performing the separation of them easily. Furthermore, in the case where the drop-off mechanism between the polymer molded articles has a certain size and maintains the drop-off function even when the intermediate position thereof is cut, or in the case where plural intermediate drop-off mechanism, such as knots (i.e., the fasteners), are provided, and the position between them is cut, the polymer molded articles at the front and back of the cut position may not be dropped off, and may be used separately as weights for traction of a living tissue.

The thickness of the connecting member is preferably from 0.01 to 3 mm in diameter. When the diameter is 0.01 mm or more, it may have a strength that withstands cutting even when the traction equipment is engaged upon passing through a narrowed portion in a digestive tract, and when the diameter is 3 mm or less, the connecting member may be cut with forceps or the like in a digestive tract, which simplifies control of the weight, the detachment and the like. In view of the factors, the thickness of the connecting member 22 is more preferably from 0.1 to 2 mm in diameter, and further preferably from 0.2 to 1.5 mm in diameter.

The material for the connecting member is preferably a substance having biocompatibility. Examples thereof include a silicone resin; a synthetic polymer, such as polylactic acid, polycaprolactone, polyvinyl alcohol, nylon, polyethylene terephthalate, polypropylene and polyglyconate; a protein, such as silk, casein, keratin, collagen and starch; and a polysaccharide, such as hyaluronic acid, chitosan and cellulose, but are not limited these materials.

The length of the medical traction device of the present invention is preferably from 10 to 200 mm in terms of the total length including the polymer molded article and the connecting member. When the length is 10 mm or more, it may be used on traction of a living tissue without interruption of an operative field. When the length is 200 mm or less, it may be easily introduced into a digestive tract. In view of the factors, the length of the medical traction device is more preferably from 20 to 150 mm, and further preferably from 50 to 100 mm. The length of the traction device means the maximum distance between two ends of the traction device when the two ends are extended linearly.

An opaque thread or an opaque medium may be incorporated in the polymer molded article and the connecting member for detecting with an X-ray after an operation in the case where the medical traction device is not recovered accidentally. In the case where the polymer molded article formed of a porous article is used, an opaque thread or an opaque medium may be incorporated in the porous medium. An opaque thread may be disposed around the polymer molded article. This may be easily applied by twisting the connecting member and an opaque thread.

Figure 26:
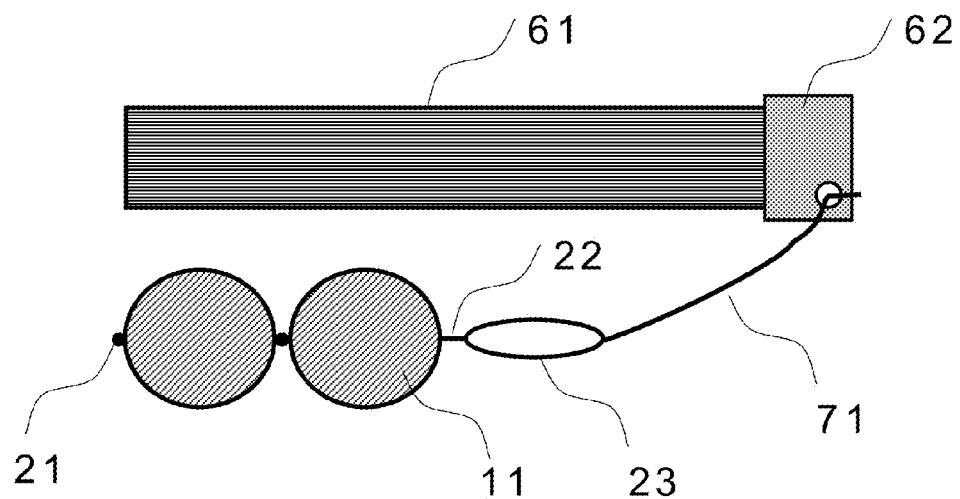
FIG. 26 is an illustration showing a use of a medical traction device according to the present invention attached to a distal end of an endoscope (distal attachment).

As shown in FIG. 26, the medical traction device of the present invention preferably has at least one second connecting member 71 for connecting the polymer molded article 11 directly or indirectly to an endoscope 61. Specifically, the endoscope 61 is preferably connected with the second connecting member 71 through a distal attachment 62 at the distal end of the endoscope.

Figure 25:
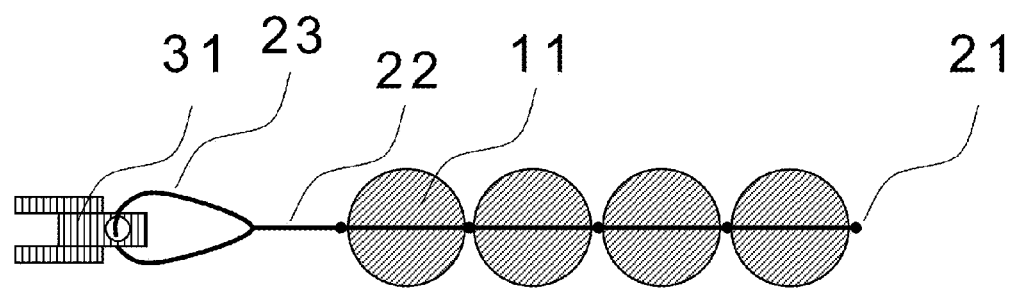
FIG. 25 is a schematic illustration showing a medical traction equipment according to the present invention.

The medical traction equipment of the present invention will be described. The medical traction equipment of the present invention contains at least the medical traction device and a grasping member, such as forceps and a clip, for attaching to a living tissue, such as a mucosa of a lesion. For example, as shown in FIG. 25, the medical traction equipment of the present invention contains a medical traction device that is connected directly to a grasping member 31 through a connecting portion (i.e., a portion in the form of a loop) 23 of a connecting member 22.

The grasping member herein is not particularly limited as far as it has a function of grasping a living tissue, and examples thereof include forceps and a clip. Examples of the material constituting the grasping member include a metal, such as iron, titanium, stainless steel and copper, and plastics, but are not limited thereto.

As an example of a method of introducing the medical traction device and the medical traction equipment of the present invention to a digestive tract, in the case where the polymer molded article of the present invention is a porous article, it may be deformed to a diameter that is smaller than the diameter of the forceps port and introduced to the digestive tract through the forceps port of the endoscope. After introducing to the digestive tract, the polymer molded article may restore the original shape due to the elasticity thereof. Thereafter, the medical traction device may be controlled to an arbitrary weight by impregnating with water. In alternative, it may be introduced into a digestive tract by attaching to the distal end of the endoscope on introducing the endoscope into the digestive tract. However, the introducing method is not limited thereto. For example, as shown in FIG. 26, the medical traction device of the present invention may be introduced to a digestive tract in such a state that the medical traction device is attached to the distal attachment 62 of the endoscope 61 at the position of the second connecting member 71.

Examples of the method of making the medical traction device and the medical traction equipment of the present invention to have a diameter that is smaller than the diameter of the forceps port include: a method of deforming the medical traction device and the medical traction equipment by introducing to the forceps port; a method of incorporating the medical traction device and the medical traction equipment of the present invention in a tube, introducing the tube through the forceps port, and taking out the traction device from the tube inside the digestive tract; and a method of compressing and fixing the medical traction device and the medical traction equipment of the present invention by applying a water soluble substance thereto, so as to have a shape having a diameter that is smaller than the diameter of the forceps port. Other methods than these methods may also be applied without limitation to these methods. The shape of the tube is preferably a cylindrical shape, but is not limited thereto. The diameter of the tube is preferably from 1 to 4 mm, but may be any diameter that is capable of passing through a forceps port. The tube may be water soluble or water insoluble. In the case of the water soluble tube, the traction equipment may be taken out by injecting water, physiological saline or the like after introducing to the digestive tract. In the case of the water insoluble tube, the traction equipment may be used after extruding from the tube with forceps or the like.

The water soluble substance used for the compression and fixation and for producing the water soluble tube is not particularly limited as far as it is harmless to humans and has a strength capable of maintaining the form of the porous article, and examples thereof include alginic acid, pullulan, starch, a cellulose compound, such as carboxymethyl cellulose, chitin, chitosan, polyglutamic acid and polyethylene glycol.

Figure 34:
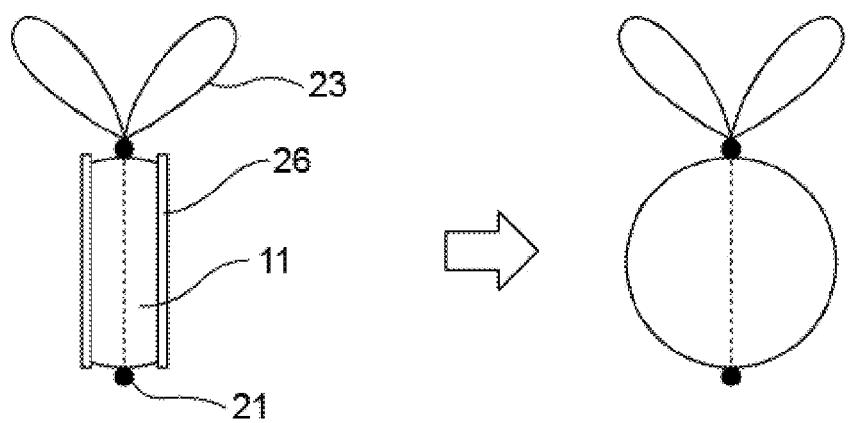
FIG. 34 is a schematic illustration showing a medical traction device according to the present invention and an illustration showing a use thereof.

For example, as shown in FIG. 34, a spherical polymer molded article 11 formed of a fibroin porous article is compressed and disposed in a tube 26. The polymer molded article 11 is taken out from the tube 26 inside the digestive tract and may be used as a traction device by injecting water.

As another method of providing a diameter that is smaller than the diameter of the forceps port, a substance that undergoes volume expansion through water absorption, such as a water absorbing polymer, may be wrapped with the polymer molded article in a sheet form formed of a porous article. A sheet polymer molded article encompassing a water absorbing polymer may be formed into a tube and introduced to a digestive tract, and after making it to be grasped to an end of a mucosa, the volume thereof may be expanded through absorption of water. The water absorbing polymer is expanded to a spherical shape by closing both the ends of the tube, and thus functions as a weight. Examples of the water absorbing polymer include a synthetic polymer, such as polyacrylic acid and polyvinyl alcohol, a polyamine, such as polyglutamic acid, and a polysaccharide, such as polyalginic acid, chitin, chitosan and carboxymethyl cellulose.

Figure 35:
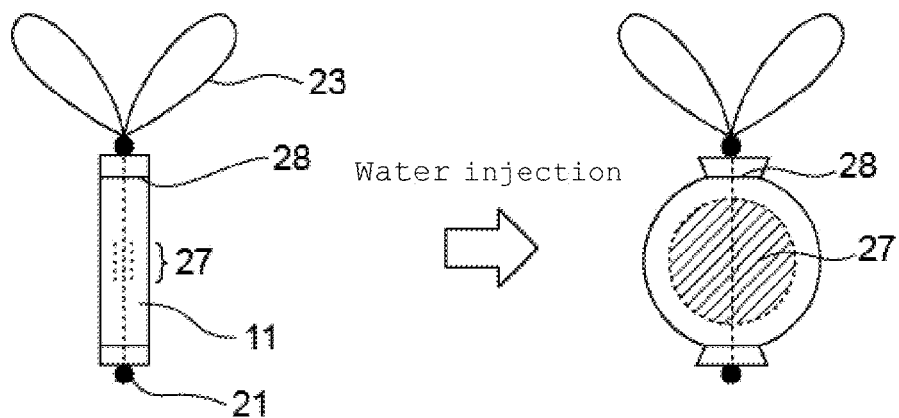
FIG. 35 is a schematic illustration showing a medical traction device according to the present invention and an illustration showing a use thereof.

For example, as shown in FIG. 35, powder of a water absorbing polymer 27 is disposed inside a polymer molded article 11 formed by rolling up a sheet fibroin porous article with both the upper and lower ends thereof being bound with a suture or the like, and a connecting portion 23 and a fastener 21 are disposed thereto. The assembly is introduced to a digestive tract, to which water is then injected, whereby the water absorbing polymer inside is expanded through absorption of water through the fibroin porous article, and the assembly may be used as a traction device.

An embodiment where the medical traction device and the medical traction equipment of the present invention are used in ESD will be described with reference to FIGS. 27 to 30.

Figure 27:
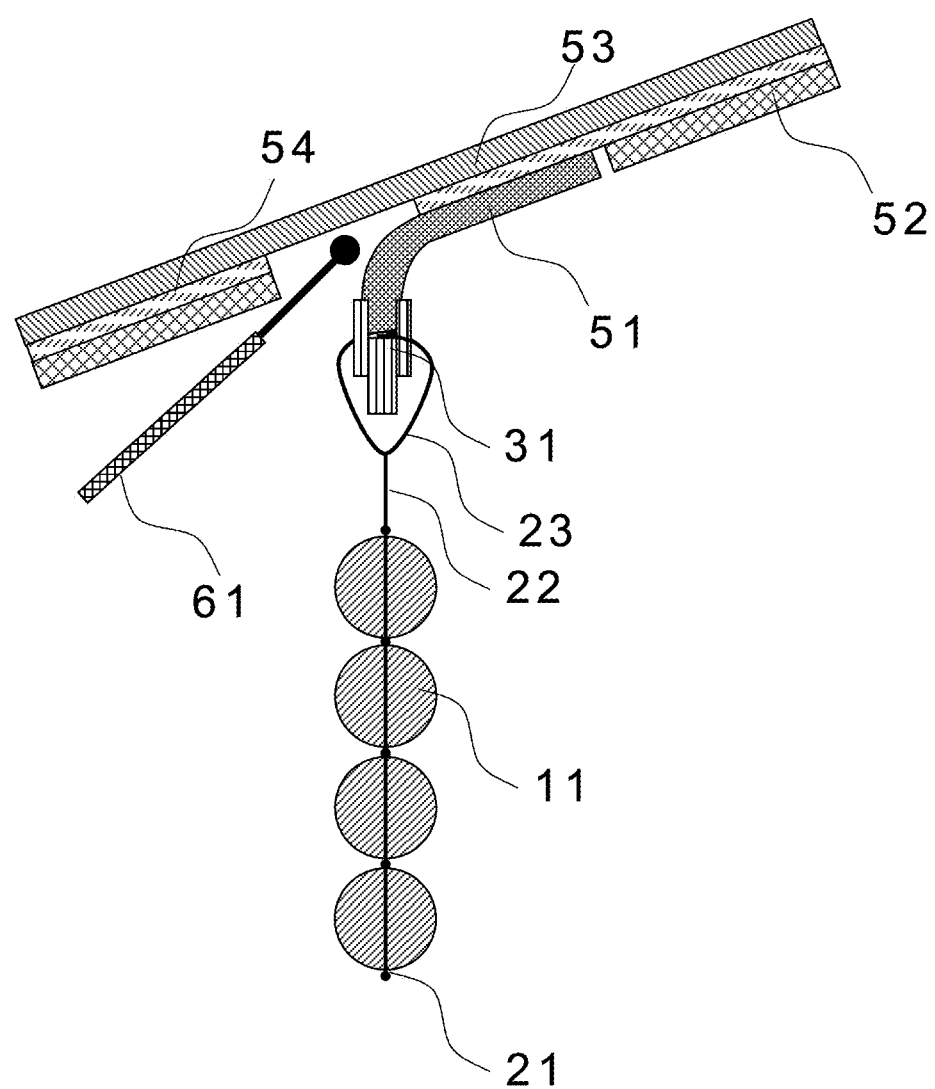
FIG. 27 is an illustration showing a use of a medical traction device according to the present invention.
Figure 28:
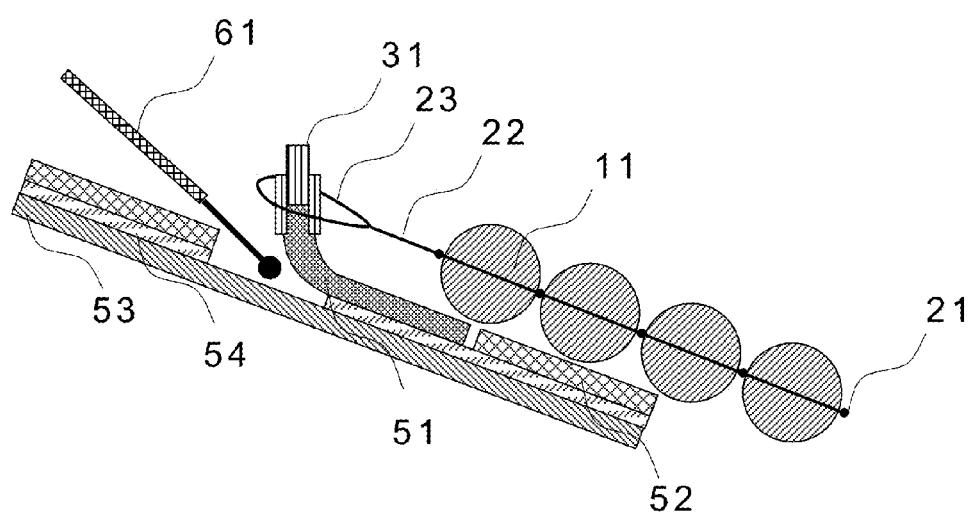
FIG. 28 is an illustration showing a use of a medical traction device according to the present invention.

FIG. 27 is a schematic illustration showing a use embodiment of the medical traction device of the present invention in ESD. In the procedure of ESD, after marking a circumference of a lesion 51, a local injection drug is injected for prominence of the lesion 51, and only a mucosa 52 of the lesion 51 is cut. Thereafter, a submucosal layer 54 is cut with a knife for dissecting the lesion 51. After dissecting the lesion 51 partly, forceps 31 are attached to the dissected portion. The connecting member 23 of the medical traction device of the present invention is fixed to the forceps 31. The medical traction device of the present invention may be disposed at an arbitrary position in a direction of tearing off the lesion 51 with the medical traction device through gravity. In alternative, the medical traction device of the present invention may be disposed at an arbitrary position by changing the body position of the patient (see FIG. 28). Before starting to cut the mucosa 52 around the lesion 51, the forceps 31 and the medical traction device of the present invention may be attached to a portion to be dissected.

The use of the medical traction device of the present invention enables observation of the submucosal layer 54 under the lesion 51 without interrupting the field of view by the lesion 51. Furthermore, when the cut of the submucosal layer 54 proceeds, the lesion 51 is rolled up through traction of the medical traction device. Accordingly, by using the medical traction device of the present invention, the procedures may be performed safely and rapidly without interrupting the operative field by the lesion 51.

Figure 29:
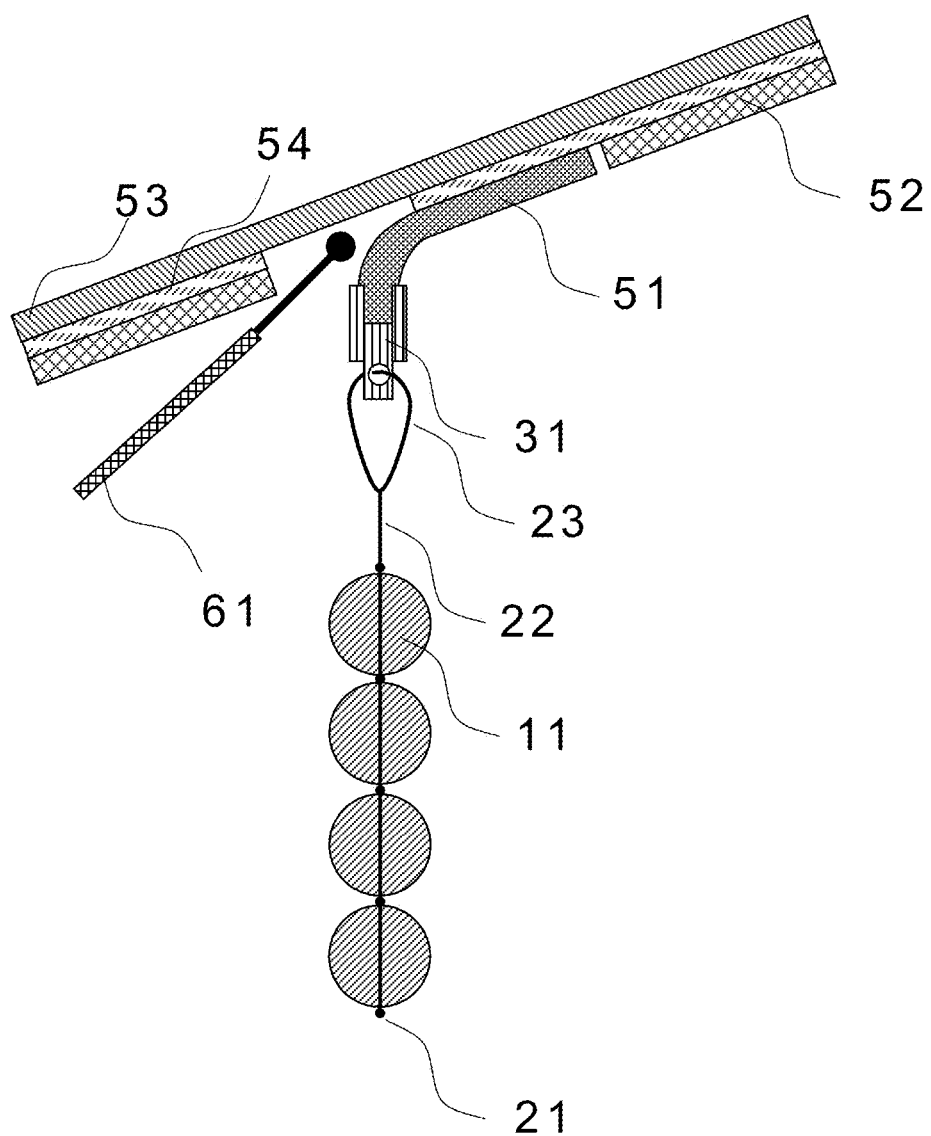
FIG. 29 is an illustration showing a use of a medical traction equipment according to the present invention.
Figure 30:
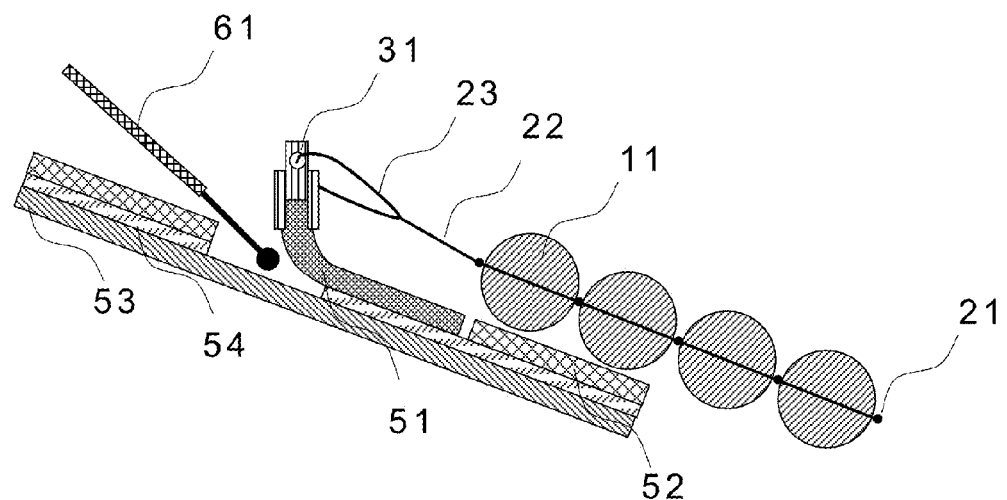
FIG. 30 is an illustration showing a use of a medical traction equipment according to the present invention.

FIGS. 29 and 30 show a use embodiment of the medical traction equipment of the present invention in ESD. A connecting portion 23 of a connecting member of a medical traction device according to the present invention has been initially connected to forceps 31 as a grasping member, and the medical traction equipment may be used after grasping a lesion 51 with the forceps 31. The basic use method thereof may be the same as those described with reference to FIGS. 27 and 28.

EXAMPLE

The present invention will be described in more detail with reference to examples below, but the present invention is not limited to the examples.

Production Examples 1 to 8 of porous articles used for the polymer molded article of the present invention are shown below.

Production Example 1

A silk fibroin aqueous solution was obtained by dissolving fibroin powder (Silkpowder IM, a trade name, produced by KB Seiren, Ltd.) in a 9 M lithium bromide aqueous solution, removing insoluble matters by centrifugal separation, and repeating dialysis with ultrapure water. The resulting silk fibroin aqueous solution was concentrated by air-drying in the dialysis tube. A lactic acid aqueous solution was added to the concentrated liquid, thereby preparing a silk fibroin solution having a silk fibroin concentration of 5% by mass and a lactic acid concentration of 2% by mass.

The silk fibroin solution was poured into a mold (inner dimension: 80 mm×40 mm×4 mm) produced with an aluminum plate, and stored in a frozen state in a low temperature thermostat chamber (EYELA NCB-3300, produced by Tokyo Rikakiki Co., Ltd.).

Upon freezing, the low temperature thermostat chamber was cooled to −5° C. in advance, and the mold having the silk fibroin solution placed therein was put in the low temperature thermostat chamber and maintained for 2 hours. Thereafter, it was cooled until the interior of the chamber reached −20° C. at a cooling speed of 3° C. per hour over 5 hours, and maintained at −20° C. for 5 hours. The frozen specimen was returned to room temperature by spontaneous melting, taken out from the mold, and removing lactic acid used therefrom by immersing in ultrapure water and exchanging ultrapure water twice per one day for three days.

As the mechanical characteristics of the resulting silk fibroin porous article, the 25% compression hardness thereof was measured in the aforementioned manner. The compression hardness is shown in Table 1. The measurement results is an average value (±standard deviation) of the results of 10 positions including arbitrary 5 positions of the porous article thus produced and arbitrary 5 positions of the porous article that is produced in another day.

A specimen for measuring the 40% compression residual strain (thickness: 10 mm, 30 mm in length×60 mm in width) was cut out from a silk porous article (60 mm×30 mm×20 mm) produced in the same manner, and the 40% compression residual strain was measured. The result is shown in Table 2.

Figure 1:
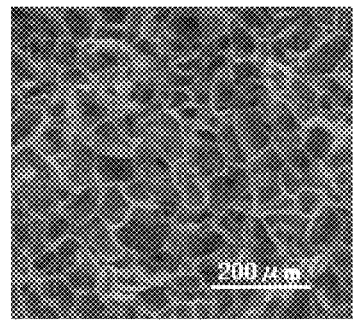
FIG. 1 is an SEM image of a polymer molded article according to the present invention.

The structure of the resulting silk fibroin porous article was observed with a scanning electron microscope. The scanning electron microscope used was XL30-FEG, produced by Philips Electronics N.V., and the measurement was performed in a low vacuum no vapor deposition mode at an acceleration voltage of 10 kV. The structure of the silk porous article was observed in the interior of the porous article exposed by cutting the porous article, but not on the surface thereof. The scanning electron micrograph of the cross section of the resulting porous article is shown in FIG. 1.

A silk porous article (60 mm×30 mm×20 mm) produced in the same manner was measured for water retention rate. The result is shown in Table 2. The water absorbing rate of the silk porous article measured was 1,300%.

Production Example 2

Figure 2:
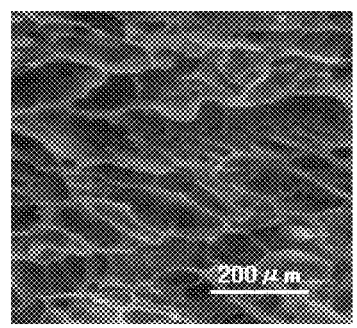
FIG. 2 is an SEM image of a polymer molded article according to the present invention.

A silk porous article was obtained in the same manner as in Production Example 1 except that ethanol was used instead of lactic acid. The 25% compression hardness evaluated in the same manner as in Production Example 1 is shown in Table 1. The scanning electron micrograph measured in the same manner as in Production Example 1 is shown in FIG. 2. The water retention rate measured in the same manner as in Production Example 1 is shown in Table 2.

Production Example 3

Figure 3:
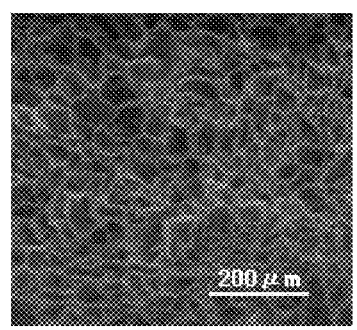
FIG. 3 is an SEM image of a polymer molded article according to the present invention.

A silk porous article was obtained in the same manner as in Production Example 1 except that succinic acid was used instead of lactic acid. The 25% compression hardness evaluated in the same manner as in Production Example 1 is shown in Table 1. The scanning electron micrograph measured in the same manner as in Production Example 1 is shown in FIG. 3. The water retention rate measured in the same manner as in Production Example 1 is shown in Table 2.

Production Example 4

Figure 4:
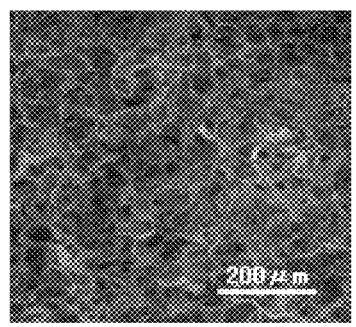
FIG. 4 is an SEM image of a polymer molded article according to the present invention.

A silk porous article was obtained in the same manner as in Production Example 1 except that acetic acid was used instead of lactic acid. The 25% compression hardness evaluated in the same manner as in Production Example 1 is shown in Table 1. The scanning electron micrograph measured in the same manner as in Production Example 1 is shown in FIG. 4. The 40% compression residual strain and the water retention rate measured in the same manner as in Production Example 1 are shown in Table 2.

Production Example 5

Figure 5:
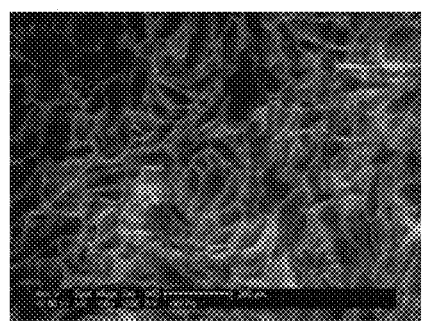
FIG. 5 is an SEM image of a polymer molded article according to the present invention.

A silk porous article was obtained in the same manner as in Production Example 1 except that L-asparaginic acid was used instead of lactic acid, and the addition amount thereof was changed to 1% by mass. The scanning electron micrograph measured in the same manner as in Production Example 1 is shown in FIG. 5.

Production Example 6

Figure 6:
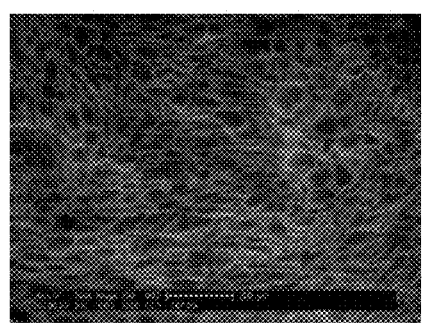
FIG. 6 is an SEM image of a polymer molded article according to the present invention.

A silk porous article was obtained in the same manner as in Production Example 1 except that L-glutamic acid was used instead of lactic acid, and the addition amount thereof was changed to 1% by mass. The 25% compression hardness evaluated in the same manner as in Production Example 1 is shown in Table 1. The scanning electron micrograph measured in the same manner as in Production Example 1 is shown in FIG. 6. The water retention rate measured in the same manner as in Production Example 1 is shown in Table 2.

Production Example 7

Figure 7:
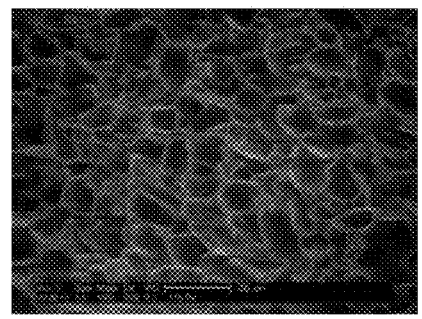
FIG. 7 is an SEM image of a polymer molded article according to the present invention.

A silk porous article was obtained in the same manner as in Production Example 1 except that L-hydroxyproline was used instead of lactic acid, and the addition amount thereof was changed to 1% by mass. The 25% compression hardness evaluated in the same manner as in Production Example 1 is shown in Table 1. The scanning electron micrograph measured in the same manner as in Production Example 1 is shown in FIG. 7.

Reference Example 1

A commercially available collagen sheet (Polymoist Mask, produced by Cognis GmbH) was used, and 10 plies of the collagen sheets were accumulated and evaluated for 25% compression hardness in the same manner as in Production Example 1. The result is shown in Table 1.

Reference Example 2

Commercially available polyurethane sponge (produced by Sumitomo 3M, Ltd.) was used, and a measurement specimen (60 mm×30 mm×20 mm) was cut therefrom and measured for water retention rate. The result is shown in Table 2.

TABLE 1

| | Additive | 25% Compression hardness (N) |
|---|---|---|
| Production Example 1 | lactic acid | 1.63 ± 0.178 |

TABLE 1-continued

| | Additive | 25% Compression hardness (N) |
|---|---|---|
| Production Example 2 | ethanol | 0.729 ± 0.250 |
| Production Example 3 | succinic acid | 0.914 ± 0.0934 |
| Production Example 4 | acetic acid | 2.11 ± 0.210 |
| Production Example 6 | L-glutamic acid | 2.54 ± 0.369 |
| Production Example 7 | L-hydroxyproline | 1.10 ± 0.0984 |
| Reference Example 1 | — | 0.281 |

TABLE 2

| | Additive | 40% Compression strain (%) | Water retention rate (%) |
|---|---|---|---|
| Production Example 1 | lactic acid | 9.89 | 98.8 |
| Production Example 2 | ethanol | — | 97.9 |
| Production Example 3 | succinic acid | — | 98.3 |
| Production Example 4 | acetic acid | 7.81 | 98.7 |
| Production Example 6 | L-glutamic acid | — | 98.4 |
| Reference Example 2 | polyurethane | — | 69.0 |

Production Example 8

A silk porous article was produced in the same manner as in the same manner as in Production Example 1 except that the dimension of the mold produced with an aluminum plate was changed to 130 mm×80 mm×12 mm (inner dimension).

As a part of nonclinical studies relating to the safety of the polymer molded article of the present invention, a primary skin irritation test and a skin sensitization test were performed. The tests were performed based on "Reliability Criteria of Application Data" (Art. No. 43, Enforcement Regulations of the Pharmaceutical Affairs Law) according to "Basic Concept on Biological Safety Tests required for Application for Approval of Production (Importation) of Medical Appliance" (Pharmaceutical Affairs Bureau Notification No. 0213001 dated Feb. 13, 2003) and "Reference Data relating to Basic Concept on Biological Safety Tests" (Examination of Medical Devices No. 36 dated Mar. 19, 2003).

The silk porous article produced in Production Example 8 was cut into a dimension of 5 mm×5 mm×5 mm as a test specimen.

Production Example 9

A silk porous article was produced in the same manner as in Production Example 1. After impregnating the silk porous article with water, the porous article was frozen and cut into a spherical shape having a diameter of 1.8 mm with a machining center (produced by Okuma Corporation), thereby forming a polymer molded article. The polymer molded article was compressed and introduced into a tube having an inner diameter of 3 mm, and a 1% aqueous solution of polyglutamic acid (produced by Nippon Poly Glu Co., Ltd.) was introduced into the tube, followed by drying.

After drying, the tube was removed to provide a compressed and fixed product. Water was injected to the compressed fixed product, thereby providing a polymer molded article having the original size.

Production Example 10

A silk porous article was produced in the same manner as in the same manner as in Production Example 1 except that the dimension of the mold produced with an aluminum plate was changed to 130 mm×80 mm×12 mm (inner dimension). The silk porous article was sliced to a sheet form having a thickness of 1 mm. The sheet was cut into a 5 cm square, and 0.2 g of powder of a crosslinked product of polyglutamic acid (produced by Nippon Poly Glu Co., Ltd.) was placed on the center thereof. The sheet was rolled up into a cylindrical form with a nylon suture (#2-0) (produced by Nitcho Kogyo Co., Ltd.) as the center, and bound with a suture at the upper and lower ends thereof, thereby providing a traction device (diameter: 2 to 3 mm).

The traction device was taken out, to which water was injected, and thus the traction device was swollen to a diameter of approximately 1.5 cm.

Primary Skin Irritation Test

An extract with physiological saline and an extract with sesame oil of the silk porous article produced in Production Example 8 were applied to a rabbit for investigating the presence of local dermal irritancy. Specifically, physiological saline or sesame oil was added to the aforementioned test piece cut out from the silk porous article produced in Production Example 8, which was extracted in an autoclave under conditions of 120° for one hour, thereby providing test liquids. Separately, the extraction solvents (i.e., physiological saline and sesame oil) were each solely processed under the same conditions, which was designated as a control liquid. The administration was performed with six male rabbits per one solvent, and the test liquid and the control liquid were applied to an intact skin and a scratched skin on the back in an amount of 0.5 mL, respectively, per one rabbit.

With the test liquid by extraction with physiological saline, very slight or slight erythema was found after one hour from the administration in three examples among six examples. The erythema was also found with physiological saline as the control liquid, and thus the result was equivalent to the control liquid. The primary irritation index was 0.3, which was determined as "ignorable irritancy".

With the extract with sesame oil, very slight erythema was found after one hour from the administration in four examples among six examples. The erythema was also found with sesame oil as the control liquid, and thus the result was equivalent to the control liquid. The primary irritation index was 0.1, which was determined as "ignorable irritancy".

Skin Sensitization Test

An extract with methanol of the silk porous article produced in Production Example 1 was investigated for the presence of sensitization to a skin of a guinea pig by using 10 male guinea pigs by Maximization Test Method.

Before performing the skin sensitization test, the extraction rates were calculated for acetone and methanol for determining a suitable extraction solvent. As a result, methanol exhibited a higher extraction rate than acetone, and thus methanol was used as an extraction solvent used in the skin sensitization test.

10 mL of methanol was added to the aforementioned test piece cut out from the silk porous article produced in Production Example 8, which was extracted at room temperature with a thermostat shaking incubator. The extraction was conducted for 24 hours or more. As control groups, a negative control group sensitized with olive oil and a positive control group sensitized with 1-chloro-2,4-dinitrobenzene were provided. The number of animals for each of the control groups was five.

In both the test liquid administration group and the negative control group, as a result of induction with 6.25, 12.5, 25, 50 and 100% solutions of the extract and acetone, no skin reaction was found at all the observation times after 24, 48 and 72 hours from the induction.

In the positive control group, on the other hand, as a result of induction with a 0.10 solution of 1-chloro-2,4-dinitrobenzene, a clear positive reaction was found in all the five examples at the observation times after 24, 48 and 72 hours from the induction.

It was determined from the test results that no substance exhibiting skin sensitization was present in the silk porous article produced in Production Example 8.

It was thus confirmed that the silk porous article produced in Production Example 8 had "ignorable irritancy" and "no substance exhibiting skin sensitization present", and thus it had a high level of safety and was favorably used as the polymer molded article of the present invention, which was a weight for traction of a living tissue to be resected under observation with an endoscope.

Example 1

A silk fibroin porous article was produced in the same manner as in Production Example 1 except that the dimension of the aluminum plate in Production Example 1 was changed to 40 mm×40 mm×20 mm (inner dimension). A cube having an edge length of 1.5 cm was cut out from the porous article and shaped into a spherical shape with scissors, thereby providing the polymer molded article of the present invention.

Subsequently, two spherical polymer molded articles are connected by penetrating with a connecting member, which was formed by bundling four silk yarns of 840 denier, by means of a sewing needle. A knot (fastener) was formed between the polymer molded articles, and thereby only one of the polymer molded articles was released on cutting the suture. Furthermore, one end of the suture was knotted to form a loop with a diameter of approximately 1 cm as a connecting portion, thereby providing the medical traction device of the present invention.

Figure 31:
FIG. 31 is a photograph showing a use of a medical traction device according to the present invention.

The medical traction device was applied to an ESD operation in a stomach of living swine as a test subject (see FIG. 31). FIG. 31 is a photograph showing an ESD operation in a stomach of living swine. The two spherical masses at the center were the silk porous articles of the present invention, which were attached to the mucosa on the upper side. The operation will be described in detail with reference to FIG. 27.

The loop portion on one end of the connecting member was attached to a hole of a disposable distal attachment (D-201-11804, produced by Olympus Corporation), which was attached to a distal end of an endoscope (Q260, produced by Olympus Corporation), and was inserted carefully to a stomach of living swine through a mouth having a flexible overtube (MD-48518, Akita Sumitomo Bakelite Co., Ltd.) attached thereto. 10 mL of physiological saline was locally injected to the submucosal layer of the stomach body with a local injection needle for an endoscope, thereby forming artificially a prominence having a diameter of approximately 2 cm, which was simulated a tumor lesion. On one end of the lesion, the mucosa was cut by ESD procedures with a precutting knife (KD-10Q-1, produced by Olympus Corporation), and the traction device released from the endoscope was fixed to one end of the cut mucosa with a rotation clip (HX-610-090SC, produced by Olympus Corporation) by means of forceps (FS-5L-1, produced by Olympus Corporation) inside the stomach.

At this time, the connecting member was in a state where it was hung down from the one end of the tumor mucosa, as shown in FIG. 27. The weight was controlled through water absorption by spraying physiological saline onto the polymer molded article from the distal end of the endoscope. Thereafter, the submucosal layer was sequentially dissected with the knife, during which the resected portion did not interrupt the field of view through traction of the mucosa every time by the connecting member. After completely dissecting the submucosal layer in the lesion, the resected lesion connected to the traction device with the clip was grasped under the endoscope and taken out through the mouth, thereby completing the operation. The operation time was approximately 7 minutes. While not used in the operation, a recovery member, such as a net or snare for recovery and a tripod, may be used for recovering the resected lesion in the case where the resected lesion has a large size like 5 cm or 10 cm.

Comparative Example 1

An ESD operation of a living swine was performed for a mucosa having the same size as in Example 1 in the same manner as in Example 1 except that an ordinary traction device was used. The mucosa often interrupted the field of view, and a certain period of time was consumed for maintaining the field of view. The operation time was approximately 30 minutes.

INDUSTRIAL APPLICABILITY

According to the polymer molded article, the medical traction device and the medical traction equipment according to the present invention, in ESD in a digestive tract, a dissected living tissue may be efficiently removed from the operative field also in a direction that is different from the moving direction of the endoscope, thereby maintaining the field of view, and the procedures are thus performed safely and rapidly.

Accordingly, by using the polymer molded article, the medical traction device and the medical traction equipment according to the present invention as a mucosal resection and dissection assisting tool, the number of ESD inapplicable cases may be reduced, for example, a flat tumor that has not been able to be resected by ESD may be resected, and furthermore, the incidence rate of complications, such as perforation, which has been ordinarily approximately 5%, is expected to be reduced to be close to 0% infinitely by the maintenance of the field of view of the operative field, the reduction of the operation time, the enhancement of the one-time resection rate, and the like.

DESCRIPTION OF THE SYMBOLS 11 polymer molded article
21 fastener (drop-off prevention mechanism)
22 connecting member
23 connecting portion
24 washer
25 cylindrical tube
26 tube
27 water absorbing polymer
28 thread
31 grasping member
51 lesion
52 mucosa
54 submucosal layer
61 endoscope
62 distal attachment
71 second connecting member

The invention claimed is:

1. A polymer molded article that is a weight for traction of a living tissue to be resected under observation with an endoscope,
   wherein the polymer molded article comprises a porous material,
   wherein the porous material is a porous material produced in such a manner that a silk fibroin aqueous solution, to which an additive is added, is frozen and then melted,
   wherein the additive is at least one member selected from the group consisting of an amino acid and an aliphatic carboxylic acid, and
   wherein the amount of the additive added is from 10 to 30 parts by mass, per 100 parts by mass of the silk fibroin.

2. The polymer molded article according to claim 1, which has elasticity.

3. The polymer molded article according to claim 2, which has a 25% compression hardness of from 0.01 to 50 N.

4. The polymer molded article according to claim 1, which has a water retention rate of from 85 to 100%.

5. The polymer molded article according to claim 1, which has a spherical shape, an ellipsoidal shape, a rotational solid of a rectangle with round edges, a polyhedral shape, a cylindrical columnar shape or a conical shape.

6. The polymer molded article according to claim 1, wherein the porous material contains silk fibroin and an additive.

7. The polymer molded article according to claim 1, wherein the additive is at least one member selected from the group consisting of acetic acid, lactic acid, succinic acid, asparaginic acid, glutamic acid and hydroxyproline.

8. The polymer molded article according to claim 1, wherein the porous material is compressed and fixed with a water soluble substance.

9. The polymer molded article according to claim 1, wherein the porous material is compressed and incorporated in a water soluble or water insoluble tube.

10. The polymer molded article according to claim 1, wherein the porous material is formed into a tube and encompasses a water absorbing polymer in the tube.

11. A medical traction device comprising the polymer molded article according to claim 1.

12. The medical traction device according to claim 11, which comprises at least one first connecting member that connects the polymer molded article directly or indirectly to a living tissue.

13. The medical traction device according to claim 12, which comprises at least one second connecting member that connects the polymer molded article directly or indirectly to an endoscope.

14. The medical traction device according to claim 13, which comprises two or more of the polymer molded articles, and the plural polymer molded articles are connected with a third connecting member.

15. The medical traction device according to claim 14, wherein at least one of the first to third connecting members is in a thread form.

16. The medical traction device according to claim 14, wherein at least one of the first to third connecting members has at least one drop-off prevention mechanism that prevents the polymer molded article from being dropped off.

17. The medical traction device according to claim 14, wherein at least one of the first to third connecting members is capable of being cut under observation with an endoscope.

18. The medical traction device according to claim 14, which is capable of being controlled to have an arbitrary weight by cutting the third connecting member between the plural polymer molded articles.

19. The medical traction device according to claim 13, wherein the first and/or second connecting member has at one end thereof a portion in a form of a loop or a hook.

20. A medical traction equipment comprising the medical traction device according to claim 12 and a grasping member for grasping a living tissue.

21. The medical traction equipment according to claim 20, wherein the medical traction device and the grasping member are connected with the first connecting member.

22. The polymer molded article according to claim 1, wherein the additive comprises at least one member selected from the group consisting of lactic acid, succinic acid, acetic acid, L-asparaginic acid, L-glutamic acid, and L-hydroxyproline.

* * * * *

UNITED STATES PATENT AND TRADEMARK OFFICE
CERTIFICATE OF CORRECTION

PATENT NO. : 9,579,092 B2
APPLICATION NO. : 13/639607
DATED : February 28, 2017
INVENTOR(S) : Kazutoshi Kobayashi et al.

It is certified that error appears in the above-identified patent and that said Letters Patent is hereby corrected as shown below:

On the Title Page

Add Item (73) as follows:
--(73) Assignee: HITACHI CHEMICAL COMPANY, LTD., Tokyo (JP)--

Signed and Sealed this
Twentieth Day of February, 2018

Andrei Iancu
*Director of the United States Patent and Trademark Office*